(12) United States Patent
Jiang et al.

(10) Patent No.: US 11,614,390 B1
(45) Date of Patent: Mar. 28, 2023

(54) REAL-TIME NONDESTRUCTIVE OBSERVATION AND TWO-PHASE SEEPAGE TEST SYSTEM FOR FRACTURE OF IN-SITU FRACTURED GAS-BEARING RESERVOIR

(71) Applicant: Chongqing University, Chongqing (CN)

(72) Inventors: Changbao Jiang, Chongqing (CN); Jiayao Wu, Chongqing (CN); Bin Xiong, Chongqing (CN); Lin Li, Chongqing (CN); Yunpeng Lei, Chongqing (CN); Yue Cheng, Chongqing (CN); Wenfeng Xu, Chongqing (CN); Chunyao Huang, Chongqing (CN)

(73) Assignee: Chongqing University, Chongqing (CN)

( * ) Notice: Subject to any disclaimer, the term of this patent is extended or adjusted under 35 U.S.C. 154(b) by 0 days.

(21) Appl. No.: 17/974,607

(22) Filed: Oct. 27, 2022

(51) Int. Cl.
  *G01N 3/12* (2006.01)
  *G01N 3/06* (2006.01)
  (Continued)

(52) U.S. Cl.
  CPC ............ *G01N 3/12* (2013.01); *G01N 3/066* (2013.01); *G01N 23/046* (2013.01);
  (Continued)

(58) Field of Classification Search
  CPC .. G01N 15/082; G01N 33/2823; G01N 25/00; G01N 33/246; G01N 13/00; G01N 3/00; G01N 23/20025; G01N 3/02; G01N 15/0806; G01N 3/18; G01N 3/10; G01N 33/24; G01N 15/08; G01N 3/12;
  (Continued)

(56) References Cited

U.S. PATENT DOCUMENTS

| 4,502,338 A * | 3/1985 | Smith | G01N 3/08 73/826 |
| 11,016,010 B1 * | 5/2021 | Li | G01N 3/36 |

(Continued)

FOREIGN PATENT DOCUMENTS

| CN | 107939364 A | 4/2018 |
| CN | 110542639 A | 12/2019 |

(Continued)

*Primary Examiner* — Brandi N Hopkins

(57) ABSTRACT

Disclosed is a real-time nondestructive observation and two-phase seepage test system for a fracture of an in-situ fractured gas-bearing reservoir, which comprises a stress loading system, a high-voltage electric pulse fracturing operation system, a water-gas two-phase seepage system and an in-situ CT scanning system; the stress loading system comprises a pressure chamber, an axial pressure loading module and a confining pressure loading module; the high-voltage electric pulse fracturing operation system comprises a high-voltage electric pulse generation module, a high-voltage electric pulse signal monitoring module and a protection module; the water-gas two-phase seepage system comprises a water-gas pressure loading module and a flow data acquisition module; and the in-situ CT scanning system comprises a radiation source, a flat panel detector and a CT scanning detection mechanism.

10 Claims, 3 Drawing Sheets

(51) Int. Cl.
*G01N 33/24* (2006.01)
*G01N 23/046* (2018.01)
*G01N 23/083* (2018.01)

(52) U.S. Cl.
CPC ......... *G01N 23/083* (2013.01); *G01N 33/241* (2013.01); *G01N 2203/0019* (2013.01); *G01N 2203/0026* (2013.01); *G01N 2203/0067* (2013.01); *G01N 2203/0617* (2013.01); *G01N 2223/04* (2013.01); *G01N 2223/419* (2013.01); *G01N 2223/616* (2013.01)

(58) Field of Classification Search
CPC .. G01N 1/286; G01N 33/241; G01N 15/0826; G01N 13/04; G01N 23/046; G01N 24/081; G01M 10/00; G01M 9/00; G06F 30/23; E21B 49/008; E21B 47/00; E21B 49/00; E21B 43/26; E21B 49/005; G01D 21/02
See application file for complete search history.

(56) References Cited

U.S. PATENT DOCUMENTS

2017/0003263 A1 1/2017 Huang
2018/0340874 A1* 11/2018 Liu ..................... G01N 33/24

FOREIGN PATENT DOCUMENTS

| CN | 111272576 A | * | 6/2020 |
| CN | 113390906 A | | 9/2021 |
| CN | 113504125 A | | 10/2021 |

* cited by examiner

REAL-TIME NONDESTRUCTIVE OBSERVATION AND TWO-PHASE SEEPAGE TEST SYSTEM FOR FRACTURE OF IN-SITU FRACTURED GAS-BEARING RESERVOIR

CROSS REFERENCE TO RELATED APPLICATIONS

This application claims foreign priority of Chinese Patent Application No. 202111445057.9, filed on Nov. 30, 2021 in the China National Intellectual Property Administration, the disclosures of all of which are hereby incorporated by reference.

TECHNICAL FIELD

The present invention relates to the field of coalbed methane (mine gas) exploitation.

BACKGROUND

In the field of coalbed permeability enhancement technologies, a high-voltage electric pulse coalbed anti-reflection technology has a series of advantages such as less energy consumption and high efficiency compared with the previous coalbed anti-reflection technologies. At present, a field application of a high-voltage electric pulse technology in increasing coalbed permeability has achieved certain effects, but a basic theoretical research on high-voltage electric pulse fractured coalbed permeability is still in an exploratory stage.

Water-gas two-phase seepage is a common situation in the process of coalbed methane exploitation. Flow laws of water and coalbed methane in a coal mass are mainly related to relative permeabilities of the water and the coalbed methane in the coalbed, and the permeabilities directly determine an effect of coalbed methane exploitation. Underground water plays an obvious role in controlling the occurrence and migration of the coalbed methane, and the seepage of the coalbed methane and the seepage of the underground water affect each other. Studying water-gas two-phase seepage characteristics of coal bearing the coalbed methane has important theoretical significance and engineering practice for the development and utilization of the coalbed methane.

Although an existing electric pulse fracturing and seepage enhancement system has achieved a research on high-voltage electric pulse fracturing of coal mass to a certain extent, in-situ real-time nondestructive visual information capture cannot be carried out on a bearing test piece in a test process, in-situ anti-reflection seepage and real-time information acquisition cannot be carried out on the bearing test piece in the test process, and an amount of information acquired in the test process is less, so that a research on an action response mechanism in a process of high-voltage electric pulse fracturing of coal mass is limited, and it is difficult to simulate a ground stress environment of a coal and rock mass deeply mined at the same time.

SUMMARY

The present invention is dedicated to developing a test system with a wider simulation range, simple operation and accurate test data, which can simulate in-situ water-gas two-phase seepage of a fracture of a gas-bearing reservoir and realize in-situ nondestructive observation.

Therefore, a technical solution employed by the present invention is that: a real-time nondestructive observation and two-phase seepage test system for a fracture of an in-situ fractured gas-bearing reservoir comprises: a stress loading system, a high-voltage electric pulse fracturing operation system, a water-gas two-phase seepage system and an in-situ CT scanning system, wherein:

the stress loading system comprises a pressure chamber, an axial pressure loading module and a confining pressure loading module; the pressure chamber has a circular tube structure, and a test piece is mounted in the center of the pressure chamber; the axial pressure loading module comprises an axial pressure pump, and first sliding rods, second sliding rods, third sliding rods, fourth sliding rods, fifth sliding rods, oil cylinders and axial pressure pipelines which are symmetrically arranged at upper and lower ends of the test piece and sequentially connected, the second sliding rod is in sliding fit with the pressure chamber, diameters of the first sliding rod, the third sliding rod and the fourth sliding rod are all smaller than a diameter of the second sliding rod, the fifth sliding rod is extended into the corresponding oil cylinder, a side wall of the oil cylinder is provided with an axial pressure channel, one end of the axial pressure pipeline is connected with the axial pressure pump and the other end of the axial pressure pipeline is connected into the corresponding oil cylinder through the axial pressure channel, and axial pressures equal up and down are provided for the test piece through all the sliding rods; and the confining pressure loading module comprises a confining pressure pump, an isolation rubber sleeve and two confining pressure pipelines, two confining pressure channels are symmetrically formed on a side wall of the pressure chamber, one end of the confining pressure pipeline is connected with the confining pressure pump and the other end of the confining pressure pipeline is connected into an inner cavity of the test piece through the corresponding confining pressure channel to provide a confining pressure around the test piece, the isolation rubber sleeve is wrapped outside the two first sliding rods and the test piece, and a sealing ring is arranged between the isolation rubber sleeve and the first sliding rod to prevent hydraulic oil from infiltrating into the test piece through upper and lower ends of the isolation rubber sleeve;

the high-voltage electric pulse fracturing operation system comprises a high-voltage electric pulse generation module, a high-voltage electric pulse signal monitoring module and a protection module; the high-voltage electric pulse generation module comprises a high-voltage pulse power supply, a high-voltage capacitor, a high-voltage electric pulse switch, a first lead segment, a second lead segment, a third lead segment, an electrode needle and a gas-guide and liquid-guide conducting bolt; the high-voltage pulse power supply charges the high-voltage capacitor through the first lead segment, the upper and lower ends of the test piece are both provided with the electrode needle and the gas-guide and liquid-guide conducting bolt, one end of the electrode needle abuts against the test piece and the other end of the electrode needle coaxially penetrates through the first sliding rod, the second sliding rod and the third sliding rod sequentially and then is inserted into a blind hole of the fourth sliding rod, one end of the gas-guide and liquid-guide conducting bolt is connected with the electrode needle and the other end of the gas-guide and liquid-guide conducting bolt transversely penetrates out of the fourth sliding rod, wherein the gas-guide and liquid-guide conducting bolt located above is connected with a positive electrode of the high-voltage capacitor through the second lead segment, and the gas-guide and liquid-guide conducting bolt located below is connected with a negative electrode of the high-voltage capacitor through the third lead segment, and the high-voltage electric pulse switch is connected in series on the second lead segment; the high-voltage electric pulse signal monitoring module comprises a Rogowski coil, a high-voltage probe and an oscilloscope, the Rogowski coil is sleeved on the third lead segment, the high-voltage probe is connected in series on the third lead segment, and monitoring signals of the Rogowski coil and the high-voltage probe are connected to the oscilloscope through a signal transmission line; and the protection module comprises an electromagnetic shielding field used for isolating high-energy static electricity generated by the high-voltage electric pulse fracturing operation system and an X-ray generated by the in-situ CT scanning system in the electromagnetic shielding field;

the water-gas two-phase seepage system comprises a water-gas pressure loading module and a flow data acquisition module, the water-gas pressure loading module comprises a gas tank, a water pressure pump, a gas pipeline, a water pressure pipeline, a water-gas pipeline and a water-gas collecting container, the diameter of the electrode needle is smaller than the inner diameter of the sliding rod through which the electrode needle penetrates to form a water-gas channel, and two water-gas channels are both tightly attached to the test piece, the gas-guide and liquid-guide conducting bolt has a hollow rod structure, an inside end of the gas-guide and liquid-guide conducting bolt located above is communicated with the water-gas channel and an outside end of the gas-guide and liquid-guide conducting bolt located above is connected with the water-gas collecting container through the water-gas pipeline, an inside end of the gas-guide and liquid-guide conducting bolt located below is communicated with the water-gas channel and an outside end of the gas-guide and liquid-guide conducting bolt located below is respectively provided with a gas inlet and a water inlet, wherein the gas inlet is connected with a gas outlet of the gas tank through the gas pipeline, and the water inlet is connected with a water outlet of the water pressure pump through the water pressure pipeline; and the flow data acquisition module comprises a gas flowmeter mounted on the gas pipeline and a liquid flowmeter mounted on the water pressure pipeline; and the in-situ CT scanning system comprises a radiation source, a flat panel detector and a CT scanning detection mechanism, the radiation source and the flat panel detector are respectively arranged on two sides of the pressure chamber, the pressure chamber is capable of being mounted on an insulating fixed base by horizontally rotating by 360°, the pressure chamber is made of a material meeting CT scanning requirements, and the flat panel detector is connected with the CT scanning detection mechanism through a data transmission line.

Beneficial Effects of the Present Invention:

(1) The stress loading system comprises the pressure chamber, the axial pressure loading module and the confining pressure loading module, except the axial pressure pump, the confining pressure pump, the axial pressure pipeline and the confining pressure pipeline, other parts form a whole core holder, the whole core holder is placed on the insulating fixed base and is capable of rotating horizontally by 360°, on this basis, in combination with the high-voltage electric pulse fracturing operation system, the water-gas two-phase seepage system and the in-situ CT scanning system, the real-time water-gas two-phase seepage test and the real time in-situ CT scanning after the high-voltage electric pulse during loading in a pressure-maintaining state can be carried out, so as to avoid influences of stress unloading and assembly and disassembly of the test piece on the test piece from interfering test results, and facilitate more accurate macro-micro analysis of a coal mass, and research results may provide advanced and reliable support for a high-voltage electric pulse coalbed anti-reflection technology and even a basic research of coalbed methane exploitation;

(2) the core holder may be detachably mounted on the insulating fixed base, and may be transferred or subjected to nuclear magnetic resonance detection in the pressure-maintaining state, so that a basis is provided for analyzing the test pieces in many aspects, thus satisfying conditions of providing more perfect basic theoretical analysis for the high-voltage electric pulse coalbed anti-reflection technology;

(3) the multi-stage sliding rods are combined with the oil cylinder to load the axial pressures equal up and down to the test piece, it is ensured that the sliding rod with a larger diameter is in sliding fit with the pressure chamber, the sliding rod with a smaller diameter can reduce an influence of pipe wall friction on axial pressure loading, and transmission of the axial pressures is realized by the hole in the side wall of the oil cylinder and the multi-stage sliding rods, which not only facilitates machining and replacement of single sliding rod, but also facilitates assembly and disassembly of the test piece in a test process; the holes spaced up and down in the pressure chamber are used as channels for supplying the confining pressure, and the isolation rubber sleeve is combined with the sealing ring to prevent the hydraulic oil from infiltrating into the test piece through the upper and lower ends of the isolation rubber sleeve, so that a structure is simple and loading is reliable; and the hole in the side wall of the oil cylinder is skillfully used for axial pressure loading, and the holes in the side wall of the pressure chamber are skillfully used for confining pressure loading, so that a whole layout is reasonable, compact, simple and easy to control, and meanwhile, the loaded confining pressure and axial pressures are high, so that a research on high-voltage electric pulse fracturing of coal mass can be carried out in a deep stress environment, wherein a maximum high-voltage electric pulse output is 100 kV and a maximum confining pressure is 60 MPa, which are far greater than the high-voltage electric pulse output of 25 KV and the maximum confining pressure lower than 10 MPa that can only be met currently;

(4) the upper and lower ends of the test piece are both provided with the electrode needle and the gas-guide and liquid-guide conducting bolt, so as to introduce a high-voltage electric pulse into the test piece, the electrode needle and the gas-guide and liquid-guide conducting bolt are both mounted by using the multi-stage transmission sliding rods, and considering an insulation problem, all sliding rods provided with the electrode needle are the high-density insulating rods; and in addition, a key part of the whole system is arranged in the electromagnetic shielding field for isolating the high-energy static electricity generated by the high-voltage electric pulse fracturing operation system, so that the system is safe and reliable; and (5) the gas-guide and liquid-guide conducting bolt is a hollow rod made of a conducting material, which can not only conduct electricity, but also conduct gas and liquid, the diameter of the electrode needle is limited to be smaller than the inner diameter of the sliding rod through which the electrode needle penetrates to form the water-gas channel, and two water-gas channels are both mounted to be tightly attached to the test piece, so as to conduct gas and liquid, and make full use of a spatial structure for layout, so that the whole system has a more compact and reasonable structure.

To sum up, an anti-reflection gas-bearing reservoir two-phase seepage test can be carried out by simulating an electric pulse action coal mass test under the conditions of different ground stresses, different voltages and the like, and simulating a physical test of high-voltage electric pulse fracturing of coal mass under a multi-physical field coupling action, and in-situ real-time scanning analysis is carried out in combination with industrial CT. An accurate and in-depth research is carried out on a development law and phase response characteristics of a pore fracture of gas-bearing coal after an action of the high-voltage electric pulse technology, which reveals an internal mechanism and an essence of multi-field coupling such as an electric field and a stress field in an acting process, and provides theoretical support and engineering parameter guidance for using high-voltage electric pulse fracturing of coal mass and improving exploitation efficiency of coalbed methane.

DETAILED DESCRIPTION

The present invention is further described hereinafter with reference to the embodiments and the drawings.

Figure 1:
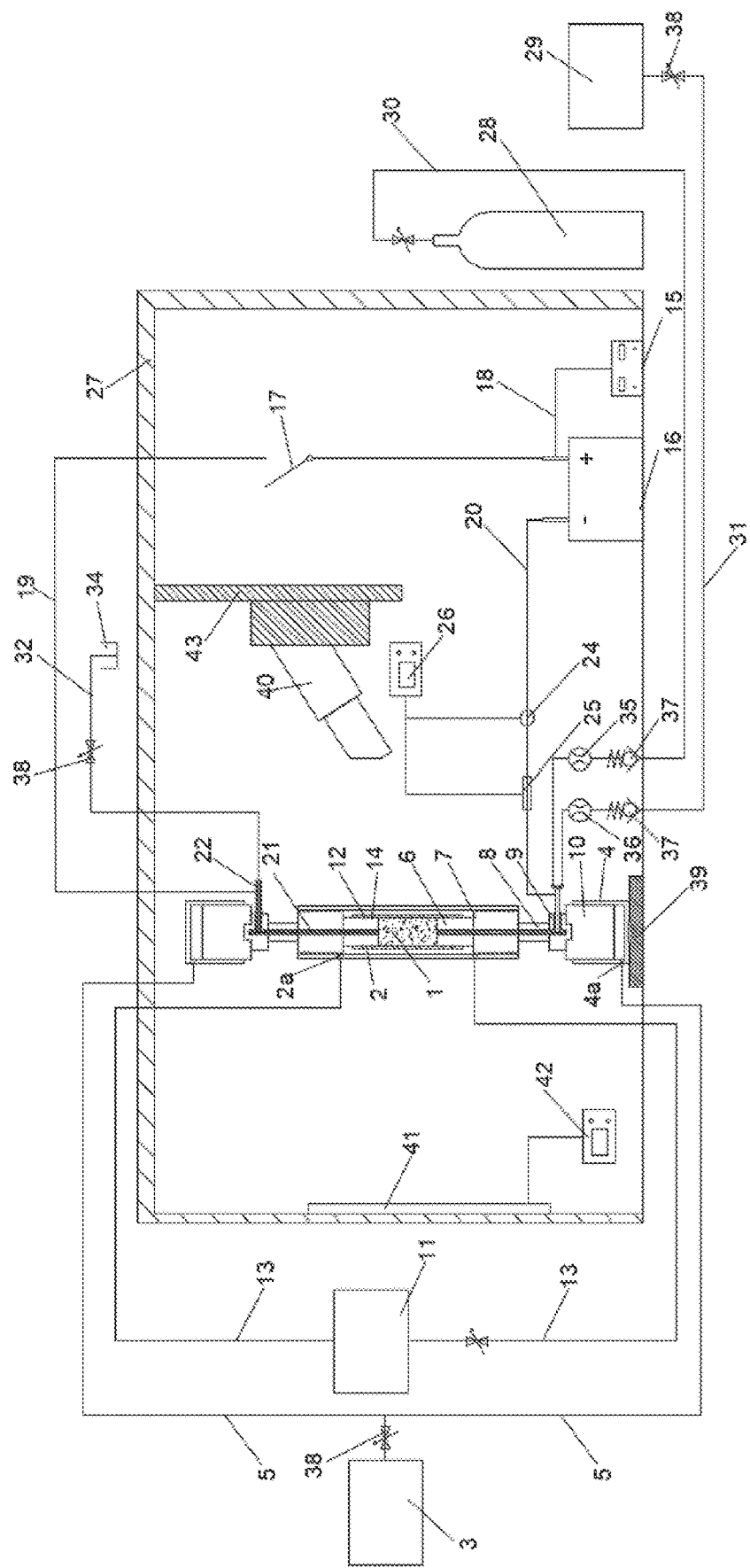
FIG. 1 is a schematic structural diagram of the present invention.
Figure 2:
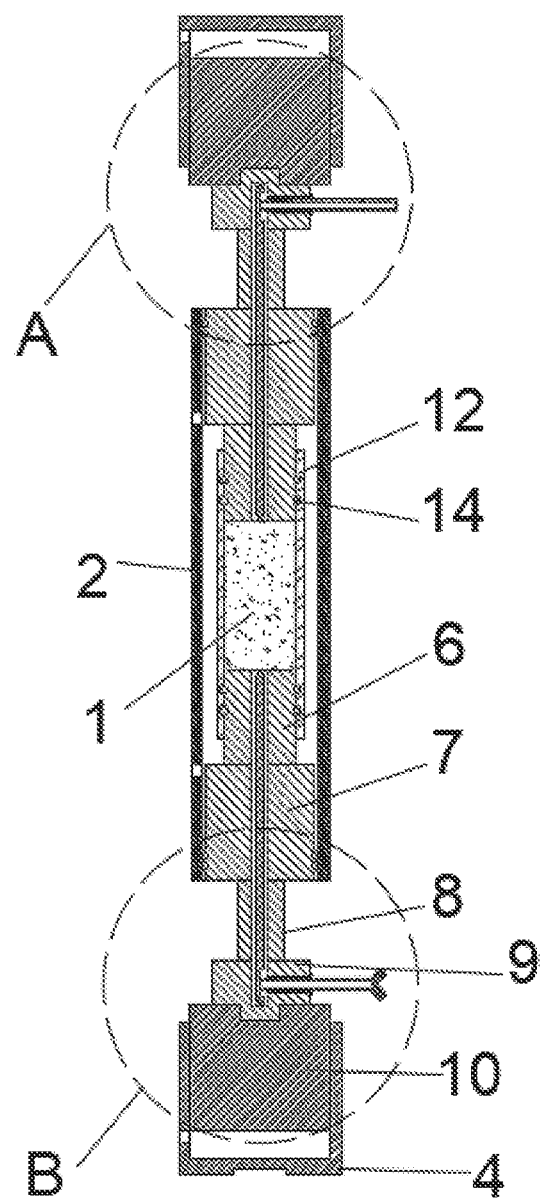
FIG. 2 is a sectional view of a pressure chamber of the present invention.
Figure 3:
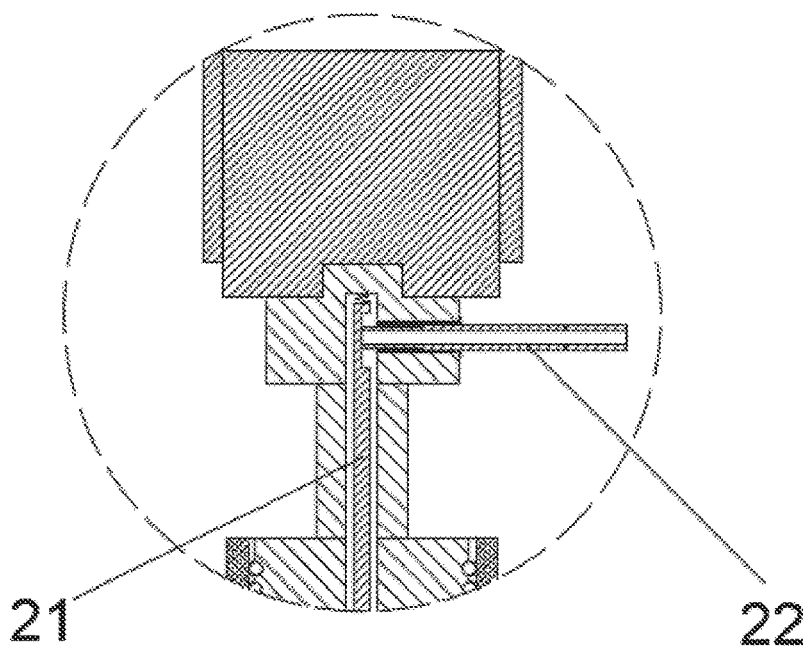
FIG. 3 is an enlarged view of a part A in FIG. 2.
Figure 4:
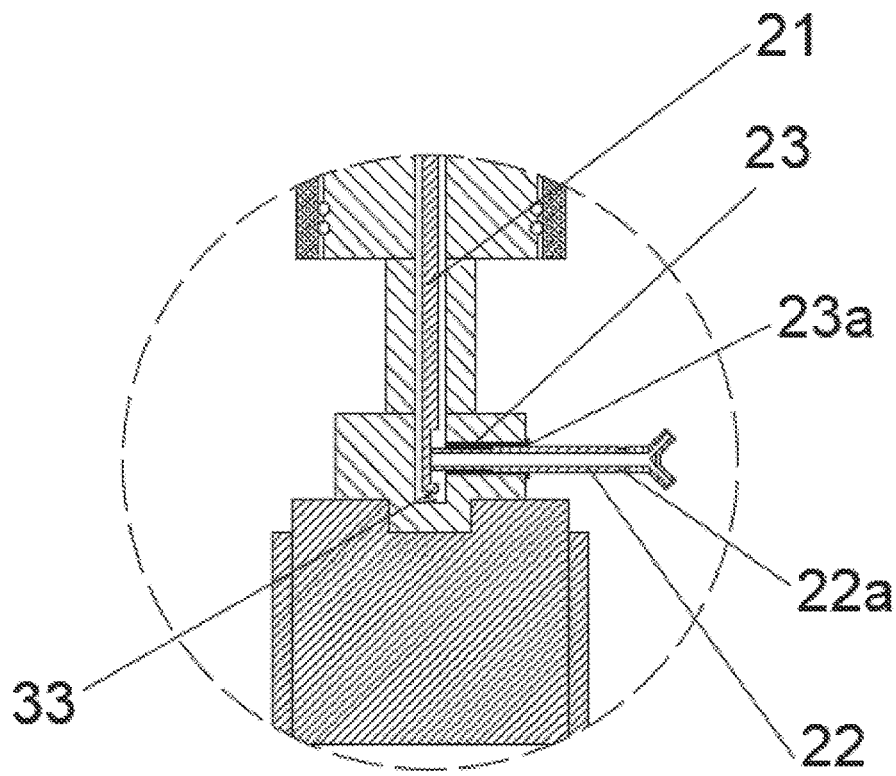
FIG. 4 is an enlarged view of a part B in FIG. 2.

With reference to FIG. 1 to FIG. 4, a real-time nondestructive observation and two-phase seepage test system for a fracture of an in-situ fractured gas-bearing reservoir mainly consists of four parts, comprising a stress loading system, a high-voltage electric pulse fracturing operation system, a water-gas two-phase seepage system and an in-situ CT scanning system.

The stress loading system mainly consists of a pressure chamber 2, an axial pressure loading module and a confining pressure loading module.

The pressure chamber 2 has a circular tube structure, and a test piece 1 is mounted in the center of the pressure chamber 2.

The axial pressure loading module consists of an axial pressure pump 3, first sliding rods 6, second sliding rods 7, third sliding rods 8, fourth sliding rods 9, fifth sliding rods 10, oil cylinders 4 and axial pressure pipelines 5 which are symmetrically arranged at upper and lower ends of the test piece 1 and sequentially connected. The second sliding rod 7 is in sliding fit with the pressure chamber 2, diameters of the first sliding rod 6, the third sliding rod 8 and the fourth sliding rod 9 are all smaller than the diameter of the second sliding rod 7, and the fifth sliding rod 10 extends into the respective corresponding oil cylinder 4. A side wall of the oil cylinder 4 is provided with an axial pressure channel 4a, one end of the axial pressure pipeline 5 is connected with the axial pressure pump 3 and the other end of the axial pressure pipeline is connected into the corresponding oil cylinder 4 through the axial pressure channel 4a, and axial pressures equal up and down are provided for the test piece 1 through all the sliding rods (the first sliding rod 6, the second sliding rod 7, the third sliding rod 8, the fourth sliding rod 9 and the fifth sliding rod 10 which sequentially transmit the axial pressure).

In order to prevent high-voltage electric energy dissipation, the first sliding rod 6, the second sliding rod 7, the third sliding rod 8 and the fourth sliding rod 9 are high-density insulating rods. In order to realize accurate control of axial pressure loading, the axial pressure pump 3 is a displacement precision injection pump with a servo control system. In addition, a contact position between the fourth sliding rod 9 and the fifth sliding rod 10 is mounted through matching between a positioning truncated cone and a positioning groove.

When the axial pressures are loaded, hydraulic oil flowing out of the axial pressure pump flows through the axial pressure pipeline to reach the oil cylinder, and the hydraulic oil reaching the oil cylinder pushes the multi-stage sliding rods to be transmitted to the test piece sequentially, thus achieving an axial pressure loading effect.

The confining pressure loading module consists of a confining pressure pump 11, an isolation rubber sleeve 12 and two confining pressure pipelines 13. Two confining pressure channels 2a are symmetrically formed on a side wall of the pressure chamber 2, one end of the confining pressure pipeline 13 is connected with the confining pressure pump 11 and the other end of the confining pressure pipeline is connected into an inner cavity of the test piece 1 through the corresponding confining pressure channel 2a to provide a confining pressure around the test piece 1. In order to enhance a sealing effect and ensure smooth progress of the test, the isolation rubber sleeve 12 is wrapped outside the two first sliding rods 6 and the test piece 1, and a sealing ring 14 is arranged between the isolation rubber sleeve 12 and the first sliding rod 6 to prevent the failure of high-voltage electrical pulse discharge to test piece caused by the immersion of hydraulic oil droplets into the test piece 1 through upper and lower ends of the isolation rubber sleeve 12.

When the confining pressure is loaded, the hydraulic oil flows through the confining pressure pipeline from the confining pressure pump to reach the pressure chamber, and after the hydraulic oil fully fills the pressure chamber, the confining pressure channel is closed, and the hydraulic oil with a pressure exerts the confining pressure around the test piece in the pressure chamber.

Preferably, before loading, a distal end of the second sliding rod 7 is flush with an end tip of the pressure chamber 2, the confining pressure channel 2a is opposite to a proximal end of the second sliding rod 7, the axial pressure channel 4a is opposite to a distal end of the fifth sliding rod 10, and a proximal end of the fifth sliding rod 10 extends out of the oil cylinder 4, thus facilitating mounting and controlling.

The high-voltage electric pulse fracturing operation system mainly consists of a high-voltage electric pulse generation module, a high-voltage electric pulse signal monitoring module and a protection module.

The high-voltage electric pulse generation module consists of a high-voltage pulse power supply 15, a high-voltage capacitor 16, a high-voltage electric pulse switch 17, a first lead segment 18, a second lead segment 19, a third lead segment 20, an electrode needle 21 and a gas-guide and liquid-guide conducting bolt 22. The high-voltage pulse power supply 15 charges the high-voltage capacitor 16 through the first lead segment 18. The upper and lower ends of the test piece 1 are both provided with the electrode needle 21 and the gas-guide and liquid-guide conducting bolt 22. One end of the electrode needle 21 abuts against the test piece 1 and the other end of the electrode needle coaxially penetrates through the first sliding rod 6, the second sliding rod 7 and the third sliding rod 8 sequentially and then is inserted into a blind hole of the fourth sliding rod 9. The blind hole is formed in the fourth sliding rod 9, and through holes are formed in the first sliding rod 6, the second sliding rod 7 and the third sliding rod 8 for the electrode needle 21 to penetrate through. One end of the gas-guide and liquid-guide conducting bolt 22 is connected with the electrode needle 21 and the other end of the gas-guide and liquid-guide conducting bolt transversely penetrates out of the fourth sliding rod 9, wherein the gas-guide and liquid-guide conducting bolt 22 located above is connected with a positive electrode of the high-voltage capacitor 16 through the second lead segment 19, and the gas-guide and liquid-guide conducting bolt 22 located below is connected with a negative electrode of the high-voltage capacitor 16 through the third lead segment 20. The high-voltage electric pulse switch 17 is connected in series on the second lead segment 19.

Preferably, the first lead segment 18, the second lead segment 19 and the third lead segment 20 are wrapped with an insulating material conforming to a 100 kV insulation standard, and joints of the second lead segment 19 and the third lead segment 20 with the gas-guide and liquid-guide conducting bolts 22 are completely wrapped with an insulating tape conforming to the 100 kV insulation standard.

In addition, an end portion of the electrode needle 21 contacted with the test piece 1 is designed into a circular truncated cone shape, and the other end of the electrode needle 21 is abutted by a compression spring 33 mounted in the blind hole of the fourth sliding rod 9, so as to ensure that the electrode needle is tightly contacted with the test piece, and avoid the electrode needle from damaging the end portion of the test piece during axial pressure loading while discharging concentratedly. The electrode needles at the upper and lower ends of the test piece should be made of a metal material with a good electrical conductivity.

The electrode needle 21 is provided with a platform for inserting the gas-guide and liquid-guide conducting bolt 22 to carry out full-lamination electric conduction, and the gas-guide and liquid-guide conducting bolt 22 is separated from the fourth sliding rod 9 by a stainless steel sealing sleeve 23. The outer diameter of the stainless steel sealing sleeve 23 is enlarged at a distal end position as a flange 23a, and the flange 23a just covers an outer wall of the fourth sliding rod 9. An inner diameter of the stainless steel sealing sleeve 23 is small at a proximal end and large at a distal end, and a stepped surface is formed on a middle position of a length. Correspondingly, a section of the gas-guide and liquid-guide conducting bolt 22 located in the fourth sliding rod 9 is also small at a proximal end and large at a distal end; and a section of the gas-guide and liquid-guide conducting bolt 22 located outside the fourth sliding rod 9 is provided with an annular groove 22a for winding and connecting the corresponding second lead segment 19 or third lead segment 20.

The high-voltage electric pulse signal monitoring module consists of a Rogowski coil 24, a high-voltage probe 25 and an oscilloscope 26. The Rogowski coil 24 is sleeved on the third lead segment 20, and the high-voltage probe 25 is connected in series on the third lead segment 20, so that circuit voltage change signals in charging and discharging processes of the high-voltage electric pulse are tested. Monitoring signals of the Rogowski coil 24 and the high-voltage probe 25 are connected to the oscilloscope 26 through a signal transmission line. The monitoring signals of the Rogowski coil and the high-voltage probe are transmitted to the oscilloscope through the signal transmission line, and waveforms of a pulse current and a voltage are displayed on an oscilloscope screen and stored as a data file, which facilitates comparative analysis of historical pulse current and voltage data, so as to determine optimal pulse current and voltage waveforms of the high-voltage electric pulse fractured test piece. The optimal pulse current and voltage waveforms are restored by adjusting a discharge form of the high-voltage electric pulse generation module subsequently, so that parameter restoration of an optimal high-voltage electric pulse fracturing effect of the test piece is realized.

Due to sensitive induction of the Rogowski coil, a placement position of the Rogowski coil should be selected as a place not easy to touch in the test process as far as possible, and meanwhile, the Rogowski coil should keep a certain distance from the second lead segment to reduce an electromagnetic interference in a data acquisition process of a pulse current signal.

A main body of the protection module is an electromagnetic shielding field 27, and since high-energy static electricity generated by the high-voltage electric pulse fracturing operation system may pose a life threat to human body, it is necessary to establish the electromagnetic shielding field to isolate the high-energy static electricity generated by the high-voltage electric pulse fracturing operation system and an X-ray generated by the in-situ CT scanning system in the test process in the electromagnetic shielding field, so as to ensure health and safety of an operator in the test process.

In addition, the pressure chamber 2 is detachably mounted on an insulating fixed base 39 by horizontally rotating by 360°, a positioning circular truncated cone is arranged at the center of a top portion of the insulating fixed base 39, and a positioning groove just for inserting the positioning truncated cone is arranged at the center of a bottom portion of the oil cylinder 4 located in the lower end.

The high-voltage pulse power supply is connected with the high-voltage capacitor through the first lead segment. Input energy to a high-voltage electric pulse circuit system may be controlled by adjusting input values of voltage and current in an input circuit according to demands in an experiment, so as to generate high-voltage electric pulses with different energies to carry out pulse discharge fracturing on the test piece. By comparing fracturing effects of different high-voltage pulse input energies on the test piece, optimal fracturing parameters of gas-bearing coalbed are determined. In the process of charging the high-voltage capacitor, charging current and voltage may be adjusted by remote operation, so as to ensure a safe and reliable test process.

The high-voltage capacitor may be combined capacitors connected in parallel, and capacitance parameters in the high-voltage electric pulse circuit are changed by changing the number of different access capacitors through a method of optional capacitance.

The high-voltage electric pulse switch is connected in series with the second lead segment, and energy release of the test piece through the high-voltage electric pulse is realized by controlling turning on and off of the high-voltage electric pulse switch. When the high-voltage electric pulse power supply charges the high-voltage capacitor with the voltage meeting the test requirements, the high-voltage electric pulse switch is turned off, so that specific high-voltage pulse energy is released by the high-voltage capacitor to act on the test piece in a short time. The number of times of pulse discharging actions of the high-voltage pulse energy on the test piece may be controlled by controlling the number of times of turning off of the high-voltage electric pulse switch, so as to realize a research on a fracturing effect of the high-voltage pulse energy at a specific frequency on the test piece.

The water-gas two-phase seepage system consists of a water-gas pressure loading module and a flow data acquisition module.

The water-gas pressure loading module mainly consists of a gas tank 28, a water pressure pump 29, a gas pipeline 30, a water pressure pipeline 31, a water-gas pipeline 32 and a water-gas collecting container 34. The diameter of the electrode needle 21 is smaller than the inner diameter of the sliding rod through which the electrode needle penetrates, so as to form a water-gas channel between the electrode needle and the sliding rod through which the electrode needle penetrates. Two water-gas channels are both tightly attached to the test piece 1. The gas-guide and liquid-guide conducting bolt 22 has a hollow rod structure, with a hollow center for water and gas to pass through. An inside end of the gas-guide and liquid-guide conducting bolt 22 located above is communicated with the water-gas channel and an outside end of the gas-guide and liquid-guide conducting bolt located above is connected with the water-gas collecting container 34 through the water-gas pipeline 32. An inside end of the gas-guide and liquid-guide conducting bolt 22 located below is communicated with the water-gas channel and an outside end of the gas-guide and liquid-guide conducting bolt located below is respectively provided with a gas inlet and a water inlet, wherein the gas inlet is connected with a gas outlet of the gas tank 28 through the gas pipeline 30, and the water inlet is connected with a water outlet of the water pressure pump 29 through the water pressure pipeline 31. The flow data acquisition module comprises a gas flowmeter 35 mounted on the gas pipeline 30 and a liquid flowmeter 36 mounted on the water pressure pipeline 31.

Preferably, one-way valves 37 are respectively mounted on the gas pipeline 30 and the water pressure pipeline 31, stop valves 38 are respectively mounted on the gas pipeline 30, the water pressure pipeline 31 and the water-gas pipeline 32, and the gas tank 28, the water pressure pump 29, the axial pressure pump 3 and the confining pressure pump 11 are mounted outside the electromagnetic shielding field 27.

In addition, the electrode needle 21 is provided with the platform for inserting the gas-guide and liquid-guide conducting bolt 22 to carry out full-lamination electric conduction, so as to carry out electric conduction. The gas-guide and liquid-guide conducting bolt 22 are separated from the fourth sliding rod 9 by the stainless steel sealing sleeve 23. The diameter of the gas-guide and liquid-guide conducting bolt 22 is greater than a width of the platform on the electrode needle 21, or a side wall of the inside end of the gas-guide and liquid-guide conducting bolt 22 is provided with a communication hole, so that a hollow center of the gas-guide and liquid-guide conducting bolt 22 is communicated with the water-gas channel The gas inlet and the water inlet of the gas-guide and liquid-guide conducting bolt 22 located below form a Y-shaped channel with the hollow center.

In the process of water-gas two-phase seepage characteristic test, coalbed methane with a certain pressure is released from the gas tank and reaches the gas inlet of the gas-guide and liquid-guide conducting bolt located below through the gas pipeline, and a water body with a pressure flows out of the pressure pump and reaches the water inlet of the gas-guide and liquid-guide conducting bolt through the water pressure pipeline. The gas with the pressure and the water body with the pressure are mixed in the hollow center of the gas-guide and liquid-guide conducting bolt, and a water-gas mixed fluid passes through the water-gas channel between the electrode needle located below and the sliding rod through which the electrode needle penetrates to reach the lower end of the test piece. Different two-phase seepage pressures are provided for the test piece by adjusting a water-gas volume ratio provided by the gas tank and the water pressure pump. The water-gas mixed fluid that seeps through the test piece reaches a top end of the test piece from a bottom end of the test piece, and then passes through the water-gas channel formed between the electrode needle located above and the sliding rod through which the electrode needle penetrates, the hollow center of the gas-guide and liquid-guide conducting bolt and the water-gas pipeline to flow into the water-gas collecting container.

In a single-phase fluid seepage characteristic test, a research on high-voltage electric pulse fracturing of coal mass under different gas pressures may be simulated by adjusting the valve of the gas tank, and a test on high-voltage electric pulse fracturing of coal mass under different fluid pressures may be carried out by adjusting an outlet flow of the water pressure pump, so that the test device has a more comprehensive capability of simulating engineering conditions.

The in-situ CT scanning system mainly consists of a radiation source 40, a flat panel detector 41 and a CT scanning detection mechanism 42. The radiation source 40 and the flat panel detector 41 are respectively arranged on two sides of the pressure chamber 2, and the flat panel detector 41 is used as a receiver. The pressure chamber 2 is capable of being mounted on an insulating fixed base 39 by horizontally rotating by 360°. In order to obtain clearer scanned image data, the pressure chamber 2 is made of a material meeting CT scanning requirements, and meanwhile, in order to meet loading requirements of the stress loading system on the test piece, the material also needs to have a high mechanical strength. The flat panel detector 41 is connected with the CT scanning detection mechanism 42 through a data transmission line.

Preferably, a double X-ray tube provided with a high-power micron focus and a high-resolution nano focus is selected as the radiation source 40, and the radiation source 40 is obliquely mounted at a lower portion of a ray tube bracket 32. An upper end of the ray tube bracket 32 is suspended at a top portion of the electromagnetic shielding field 27, and the flat panel detector 41 is mounted on a side wall of the electromagnetic shielding field 27. After a ray of the radiation source 40 penetrates through the pressure chamber 2, and then, is received by the flat panel detector 41 to form a scanned image on the CT scanning detection mechanism 42.

Tiny details below 0.5 μm may be observed through the X-ray tube, so that not only a small-size test piece can be scanned, but also a large-size or irregular test piece can be scanned and imaged. In the scanning process, the axial pressure channel and the confining pressure channel of the pressure chamber are closed, so that the test piece in the pressure chamber maintains a stable stress environment, and the insulating fixed base is controlled to drive the pressure chamber to rotate horizontally by 360°, and data is collected every time the pressure chamber rotates by an angle. After completing rotation, scanning data collection is completed at the same time.

In the in-situ CT scanning system, the receiver is a flat panel detector, and energy of the X-ray emitted from the ray tube is attenuated after penetrating through the pressure chamber. After the attenuated X-ray is received by the flat panel detector, images with different shadings are left on a negative plate of the flat panel detector. The data is transmitted to a CT scanning and detection institution through the data transmission line, and is visually displayed as a scanned picture of the test piece after data processing.

The invention claimed is:

1. A real-time nondestructive observation and two-phase seepage test system for a fracture of an in-situ fractured gas-bearing reservoir, comprising: a stress loading system, a high-voltage electric pulse fracturing operation system, a water-gas two-phase seepage system and an in-situ CT scanning system, wherein:

the stress loading system comprises a pressure chamber, an axial pressure loading module and a confining pressure loading module; the pressure chamber has a circular tube structure, and a test piece is mounted in the center of the pressure chamber; the axial pressure loading module comprises an axial pressure pump, and first sliding rods, second sliding rods, third sliding rods, fourth sliding rods, fifth sliding rods, oil cylinders and axial pressure pipelines which are symmetrically arranged at upper and lower ends of the test piece and sequentially connected, the second sliding rod is in sliding fit with the pressure chamber, diameters of the first sliding rod, the third sliding rod and the fourth sliding rod are all smaller than a diameter of the second sliding rod, the fifth sliding rod is extended into the corresponding oil cylinder, a side wall of the oil cylinder is provided with an axial pressure channel, one end of the axial pressure pipeline is connected with the axial pressure pump and the other end of the axial pressure pipeline is connected into the corresponding oil cylinder through the axial pressure channel, and axial pressures equal up and down are provided for the test piece through all the sliding rods; and the confining pressure loading module comprises a confining pressure pump, an isolation rubber sleeve and two confining pressure pipelines, two confining pressure channels are symmetrically formed on a side wall of the pressure chamber, one end of the confining pressure pipeline is connected with the confining pressure pump and the other end of the confining pressure pipeline is connected into an inner cavity of the test piece through the corresponding confining pressure channel to provide a confining pressure around the test piece, the isolation rubber sleeve is wrapped outside the two first sliding rods and the test piece, and a sealing ring is arranged between the isolation rubber sleeve and the first sliding rod to prevent hydraulic oil from infiltrating into the test piece through upper and lower ends of the isolation rubber sleeve;

the high-voltage electric pulse fracturing operation system comprises a high-voltage electric pulse generation module, a high-voltage electric pulse signal monitoring module and a protection module; the high-voltage electric pulse generation module comprises a high-voltage pulse power supply, a high-voltage capacitor, a high-voltage electric pulse switch, a first lead segment, a second lead segment, a third lead segment, an electrode needle and a gas-guide and liquid-guide conducting bolt; the high-voltage pulse power supply charges the high-voltage capacitor through the first lead segment, the upper and lower ends of the test piece are both provided with the electrode needle and the gas-guide and liquid-guide conducting bolt, one end of the electrode needle abuts against the test piece and the other end of the electrode needle coaxially penetrates through the first sliding rod, the second sliding rod and the third sliding rod sequentially and then is inserted into a blind hole of the fourth sliding rod, one end of the gas-guide and liquid-guide conducting bolt is connected with the electrode needle and the other end of the gas-guide and liquid-guide conducting bolt transversely penetrates out of the fourth sliding rod, wherein the gas-guide and liquid-guide conducting bolt located above is connected with a positive electrode of the high-voltage capacitor through the second lead segment, and the gas-guide and liquid-guide conducting bolt located below is connected with a negative electrode of the high-voltage capacitor through the third lead segment, and the high-voltage electric pulse switch is connected in series on the second lead segment; the high-voltage electric pulse signal monitoring module comprises a Rogowski coil, a high-voltage probe and an oscilloscope, the Rogowski coil is sleeved on the third lead segment, the high-voltage probe is connected in series on the third lead segment, and monitoring signals of the Rogowski coil and the high-voltage probe are connected to the oscilloscope through a signal transmission line; and the protection module comprises an electromagnetic shielding field used for isolating high-energy static electricity generated by the high-voltage electric pulse fracturing operation system and an X-ray generated by the in-situ CT scanning system in the electromagnetic shielding field;

the water-gas two-phase seepage system comprises a water-gas pressure loading module and a flow data acquisition module, the water-gas pressure loading module comprises a gas tank, a water pressure pump, a gas pipeline, a water pressure pipeline, a water-gas pipeline and a water-gas collecting container, the diameter of the electrode needle is smaller than the inner diameter of the sliding rod through which the electrode needle penetrates to form a water-gas channel, and two water-gas channels are both tightly attached to the test piece, the gas-guide and liquid-guide conducting bolt has a hollow rod structure, an inside end of the gas-guide and liquid-guide conducting bolt located above is communicated with the water-gas channel and an outside end of the gas-guide and liquid-guide conducting bolt located above is connected with the water-gas collecting container through the water-gas pipeline, an inside end of the gas-guide and liquid-guide conducting bolt located below is communicated with the water-gas channel and an outside end of the gas-guide and liquid-guide conducting bolt located below is respectively provided with a gas inlet and a water inlet, wherein the gas inlet is connected with a gas outlet of the gas tank through the gas pipeline, and the water inlet is connected with a water outlet of the water pressure pump through the water pressure pipeline; and the flow data acquisition module comprises a gas flowmeter mounted on the gas pipeline and a liquid flowmeter mounted on the water pressure pipeline; and the in-situ CT scanning system comprises a radiation source, a flat panel detector and a CT scanning detection mechanism, the radiation source and the flat panel detector are respectively arranged on two sides of the pressure chamber, the pressure chamber is capable of being mounted on an insulating fixed base by horizontally rotating by 360°, the pressure chamber is made of a material meeting CT scanning requirements, and the flat panel detector is connected with the CT scanning detection mechanism through a data transmission line.

2. The real-time nondestructive observation and two-phase seepage test system for the fracture of the in-situ fractured gas-bearing reservoir according to claim 1, wherein a double X-ray tube provided with a high-power micron focus and a high-resolution nano focus is selected as the radiation source, the radiation source is obliquely mounted at a lower portion of a ray tube bracket, an upper end of the ray tube bracket is suspended at a top portion of the electromagnetic shielding field, the flat panel detector is mounted on a side wall of the electromagnetic shielding field, and after a ray of the radiation source penetrates through the pressure chamber, and then, is received by the flat panel detector to form a scanned image on the CT scanning detection mechanism.

3. The real-time nondestructive observation and two-phase seepage test system for the fracture of the in-situ fractured gas-bearing reservoir according to claim 1, wherein the electrode needle is provided with a platform for inserting the gas-guide and liquid-guide conducting bolt to carry out full-lamination electric conduction, and the gas-guide and liquid-guide conducting bolt is separated from the fourth sliding rod by a stainless steel sealing sleeve; a diameter of the gas-guide and liquid-guide conducting bolt is greater than a width of the platform on the electrode needle, or a side wall of the inside end of the gas-guide and liquid-guide conducting bolt is provided with a communication hole, so that a hollow center of the gas-guide and liquid-guide conducting bolt is communicated with the water-gas channel; and the gas inlet and the water inlet of the gas-guide and liquid-guide conducting bolt located below form a Y-shaped channel with the hollow center.

4. The real-time nondestructive observation and two-phase seepage test system for the fracture of the in-situ fractured gas-bearing reservoir according to claim 3, wherein an outer diameter of the stainless steel sealing sleeve is enlarged at a distal position as a flange, and the flange just covers an outer wall of the fourth sliding rod; the inner diameter of the stainless steel sealing sleeve is small at a proximal end and large at a distal end, and a stepped surface is formed on a middle position of a length; correspondingly, a section of the gas-guide and liquid-guide conducting bolt located in the fourth sliding rod is also small at a proximal end and large at a distal end; and a section of the gas-guide and liquid-guide conducting bolt located outside the fourth sliding rod is provided with an annular groove for winding and connecting the corresponding second lead segment or third lead segment.

5. The real-time nondestructive observation and two-phase seepage test system for the fracture of the in-situ fractured gas-bearing reservoir according to claim 1, wherein the first sliding rod, the second sliding rod, the third sliding rod and the fourth sliding rod are high-density insulating rods, and the axial pressure pump is a displacement precision injection pump with a servo control system.

6. The real-time nondestructive observation and two-phase seepage test system for the fracture of the in-situ fractured gas-bearing reservoir according to claim 1, wherein the first lead segment, the second lead segment and the third lead segment are wrapped with an insulating material conforming to a 100 kV insulation standard, and joints of the second lead segment and the third lead segment with the gas-guide and liquid-guide conducting bolts are completely wrapped with an insulating tape conforming to the 100 kV insulation standard.

7. The real-time nondestructive observation and two-phase seepage test system for the fracture of the in-situ fractured gas-bearing reservoir according to claim 1, wherein an end portion of the electrode needle contacted with the test piece is designed into a circular truncated cone shape, and the other end of the electrode needle is abutted by a compression spring mounted in the blind hole of the fourth sliding rod.

8. The real-time nondestructive observation and two-phase seepage test system for the fracture of the in-situ fractured gas-bearing reservoir according to claim 1, wherein a positioning circular truncated cone is arranged at the center of a top portion of the insulating fixed base, and a positioning groove just for inserting the positioning circular truncated cone is arranged at a center of a bottom portion of the oil cylinder located in the lower end.

9. The real-time nondestructive observation and two-phase seepage test system for the fracture of the in-situ fractured gas-bearing reservoir according to claim 1, wherein a contact position between the fourth sliding rod and the fifth sliding rod is mounted through matching between a positioning truncated cone and a positioning groove.

10. The real-time nondestructive observation and two-phase seepage test system for the fracture of the in-situ fractured gas-bearing reservoir according to claim 1, wherein before loading, a distal end of the second sliding rod is flush with an end tip of the pressure chamber, the confining pressure channel is opposite to a proximal end of the second sliding rod, the axial pressure channel is opposite to a distal end of the fifth sliding rod, and a proximal end of the fifth sliding rod extends out of the oil cylinder.

* * * * *